(12) United States Patent
Jin (10) Patent No.: US 9,665,990 B2
(45) Date of Patent: May 30, 2017

(54) IMAGE DISPLAY TO DISPLAY 3D IMAGE AND SECTIONAL IMAGES

(71) Applicant: Ewoosoft Co., Ltd., Gyeonggi-do (KR)

(72) Inventor: Youngkyu Jin, Gyeonggi-do (KR)

(73) Assignee: Ewoosoft Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/766,747

(22) PCT Filed: Feb. 8, 2014

(86) PCT No.: PCT/KR2014/001080
§ 371 (c)(1),
(2) Date: Aug. 8, 2015

(87) PCT Pub. No.: WO2014/123395
PCT Pub. Date: Aug. 14, 2014

(65) Prior Publication Data
US 2015/0379780 A1    Dec. 31, 2015

(30) Foreign Application Priority Data
Feb. 8, 2013   (KR) ........................ 10-2013-0014496

(51) Int. Cl.
*G06T 19/20*    (2011.01)
*A61B 6/14*    (2006.01)
(Continued)

(52) U.S. Cl.
CPC .............. *G06T 19/20* (2013.01); *A61B 6/032* (2013.01); *A61B 6/14* (2013.01); *A61B 6/463* (2013.01);
(Continued)

(58) Field of Classification Search
None
See application file for complete search history.

(56) References Cited

U.S. PATENT DOCUMENTS 5,371,778 A    12/1994  Yanof et al.
5,734,384 A    3/1998   Yanof et al.
(Continued)

FOREIGN PATENT DOCUMENTS

KR    20-0303415 Y1    2/2003
KR    10-0947826 B1    3/2010
(Continued)

OTHER PUBLICATIONS

Korean Intellectual Property Office, International Search Report of International Application No. PCT/KR2014/001081, May 20, 2014.
(Continued)

*Primary Examiner* — Michelle Chin
(74) *Attorney, Agent, or Firm* — IP Legal Services, LLC (57) ABSTRACT

The disclosure is related to displaying a three dimensional image and corresponding sectional images. A display device may include a data storage, an input interface, an image display, and a processor. The data storage may store image data. The input interface may receive position information of a first image point from a user. The image display may display a 3D image in a first display region and a sectional image of the 3D image in a second display region of the screen. The processor may generate the 3D image data to display the 3D image by locating the first image point of the 3D image at a first position in the first display region and the sectional image data to display the sectional image of the 3D image by locating a second image point of the sectional image at a second position in the second display region.

20 Claims, 12 Drawing Sheets

(51) Int. Cl.
*A61B 6/03* (2006.01)
*G09G 5/14* (2006.01)
*A61B 6/00* (2006.01)
*G06T 7/00* (2017.01)
*G06T 15/00* (2011.01)
*G06T 17/00* (2006.01)

(52) U.S. Cl.
CPC .............. *A61B 6/466* (2013.01); *A61B 6/467* (2013.01); *A61B 6/5223* (2013.01); *G06T 7/0012* (2013.01); *G06T 15/00* (2013.01); *G06T 17/00* (2013.01); *G09G 5/14* (2013.01); *G06T 2207/10081* (2013.01); *G06T 2207/10116* (2013.01); *G06T 2207/30036* (2013.01); *G06T 2210/41* (2013.01); *G06T 2219/028* (2013.01); *G09G 2380/08* (2013.01)

(56) References Cited

U.S. PATENT DOCUMENTS

| | | |
|---|---|---|
| 6,633,789 B1 | 10/2003 | Nikolskiy et al. |
| 6,664,986 B1 | 12/2003 | Kopelman et al. |
| 8,199,988 B2 | 6/2012 | Marshall et al. |
| 2006/0203959 A1 | 9/2006 | Spartiotis et al. |
| 2007/0025642 A1 | 2/2007 | Buckland et al. |
| 2007/0287916 A1 | 12/2007 | Kim et al. |
| 2008/0019477 A1 | 1/2008 | Spartiotis et al. |
| 2008/0063139 A1 | 3/2008 | Pantsar et al. |
| 2008/0181477 A1 | 7/2008 | Izatt et al. |
| 2009/0191503 A1 | 7/2009 | Matov et al. |
| 2009/0316966 A1 | 12/2009 | Marshall et al. |
| 2009/0323891 A1 | 12/2009 | Borghese et al. |
| 2010/0142673 A1 | 6/2010 | Pantsar et al. |
| 2010/0208866 A1 | 8/2010 | Spartiotis et al. |
| 2010/0246761 A1 | 9/2010 | Pantsar et al. |
| 2010/0255445 A1 | 10/2010 | Gantes |
| 2011/0033026 A1 | 2/2011 | Ulrici et al. |
| 2011/0075946 A1 | 3/2011 | Buckland et al. |
| 2011/0102549 A1 | 5/2011 | Takahashi |
| 2011/0144499 A1 | 6/2011 | Yoo et al. |
| 2011/0172534 A1 | 7/2011 | Kim |
| 2011/0282205 A1 | 11/2011 | Kim |
| 2013/0202176 A1 | 8/2013 | Izatt et al. |
| 2013/0230818 A1 | 9/2013 | Matov et al. |

FOREIGN PATENT DOCUMENTS

| | | |
|---|---|---|
| KR | 10-1117930 B1 | 2/2012 |
| KR | 10-1126891 B1 | 3/2012 |
| KR | 10-1183767 B1 | 9/2012 |
| WO | 98/53428 A1 | 11/1998 |

OTHER PUBLICATIONS

Korean Intellectual Property Office, Written Opinion of International Application No. PCT/KR2014/001081, May 20, 2014.
Korean Intellectual Property Office, International Search Report of International Application No. PCT/KR2014/001080, May 23, 2014.
Korean Intellectual Property Office, Written Opinion of International Application No. PCT/KR2014/001080, May 23, 2014.

Fig. 1

(Related Art)

Fig. 2

(Related Art)

(Related Art)

Fig. 5

(Related Art)

Fig. 6

(Related Art)

Fig. 7

(Related Art)

Fig. 8

(Related Art)

IMAGE DISPLAY TO DISPLAY 3D IMAGE AND SECTIONAL IMAGES

CROSS REFERENCE TO RELATED APPLICATIONS

This application is a National Stage Patent Application of PCT International Patent Application No. PCT/KR2014/001080 (filed on Feb. 8, 2014) under 35 U.S.C. §371, which claims priority to Korean Patent Application No. 10-2013-0014496 (filed on Feb. 8, 2013), the teachings of which are incorporated herein in their entireties by reference.

TECHNICAL FIELD

The present disclosure relates to an image display, and more particularly to an image display capable of displaying a three-dimensional image and sectional images concurrently in defined relation.

BACKGROUND ART

An X-ray computerized tomography (CT) imaging apparatus emits X-rays to an object and detects the X-rays transmitted through the object using an X-ray detector. Based on the detected X-rays, the X-ray CT imaging apparatus generates image data. The X-ray CT imaging apparatus produces and displays a three-dimensional (3D) image and corresponding sectional images (e.g., axial images, sagittal images, and coronal images) based on the generated image data.

Figure 1:
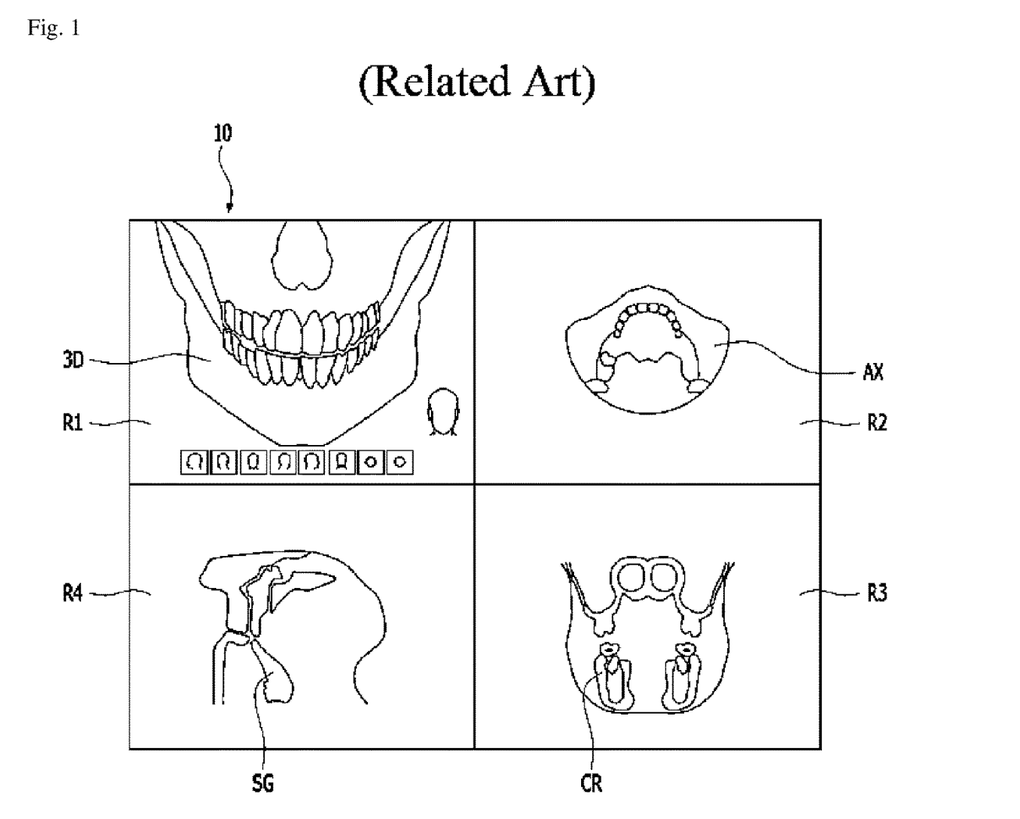
FIG. 1 is a schematic diagram showing an example of displaying a three-dimensional (3D) image and sectional image on a screen of a typical X-ray image display device.

FIG. 1 illustrates dental X-ray images displayed on a display of a typical image display apparatus. As shown in FIG. 1, screen 10 includes four image display regions R1, R2, R3 and R4 for displaying a volume (e.g., 3-dimensional) image 3D, an axial image AX, a coronal image CR, and a sagittal image SG. Initially, these four images are displayed with a default display condition. In order to examine a tooth of interest accurately, a user (e.g., dentist) should change display conditions of the four images.

Figure 2:
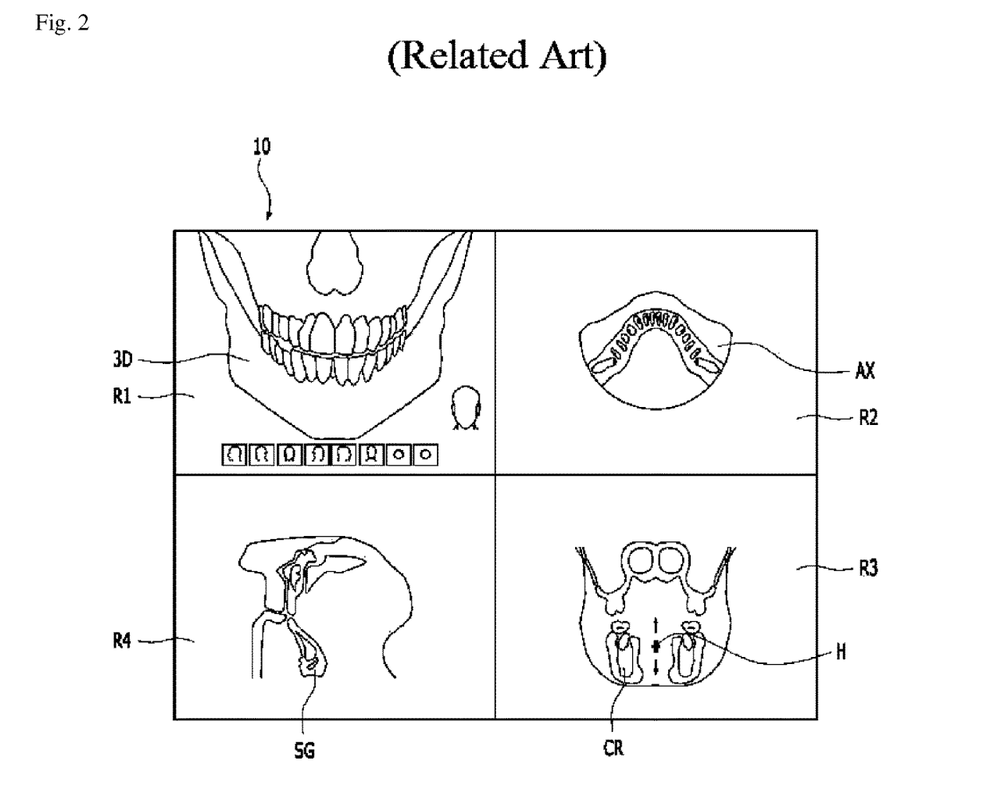
FIG. 2 is a schematic diagram showing a step of specifying a height H of a tooth of interest on a coronal image CR displayed on a screen of a typical X-ray image display device.
Figure 3:
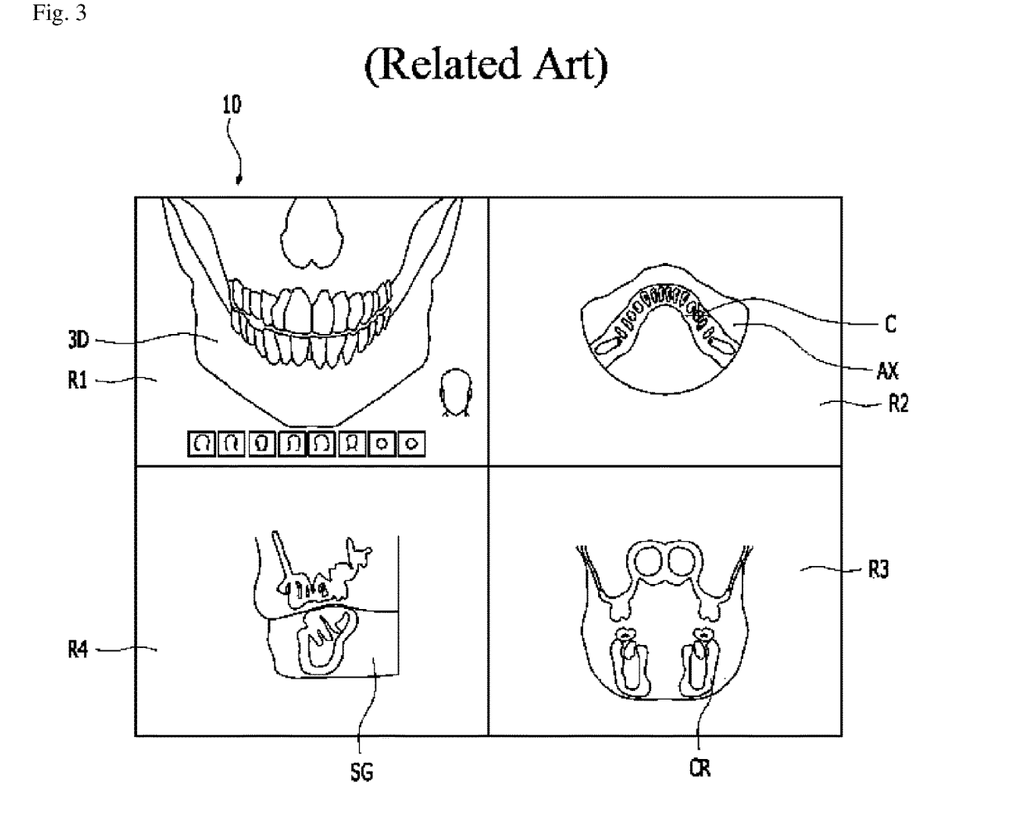
FIG. 3 is a schematic diagram showing a step of specifying a center C of a tooth of interest on an axial image AX.
Figure 4:
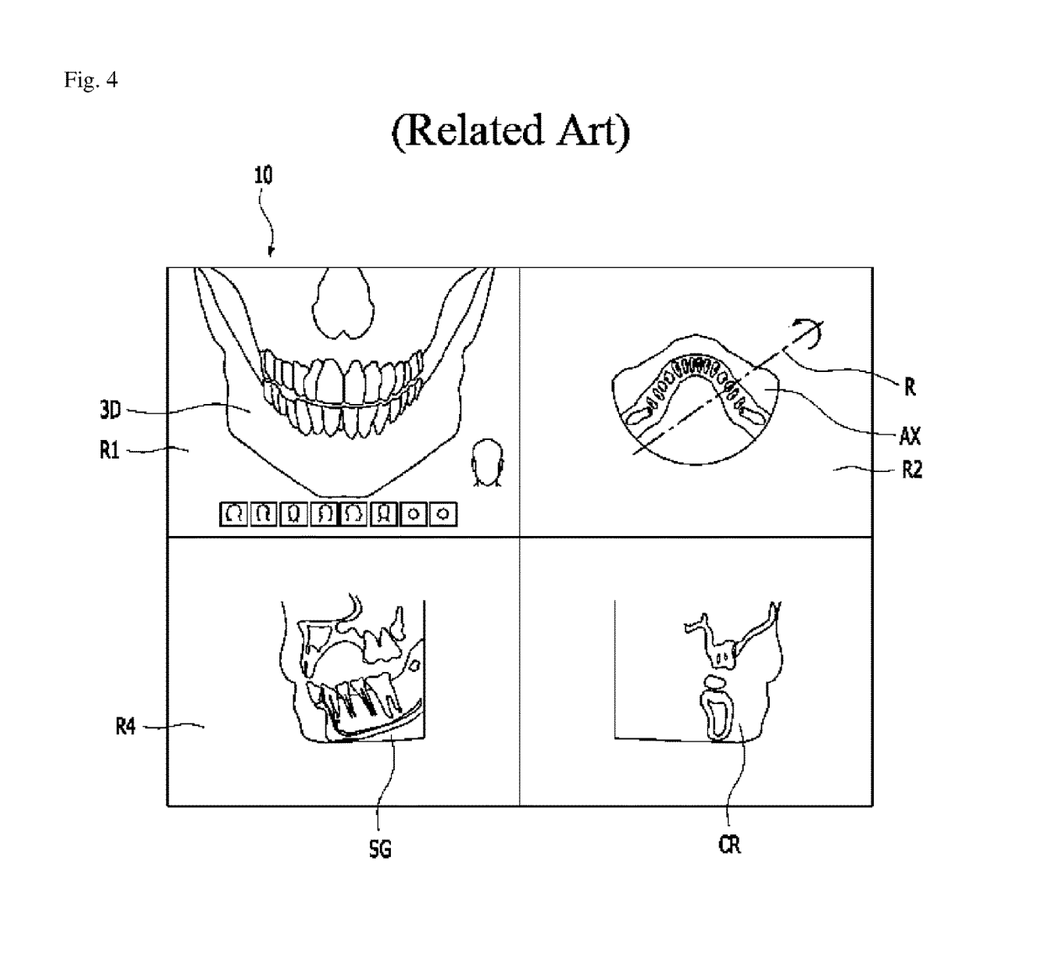
FIG. 4 is a schematic diagram showing a step of rotating one of two axes, perpendicular each other at the center of a tooth of interest, by a rotating angle R, on an axial image AX.
Figure 5:
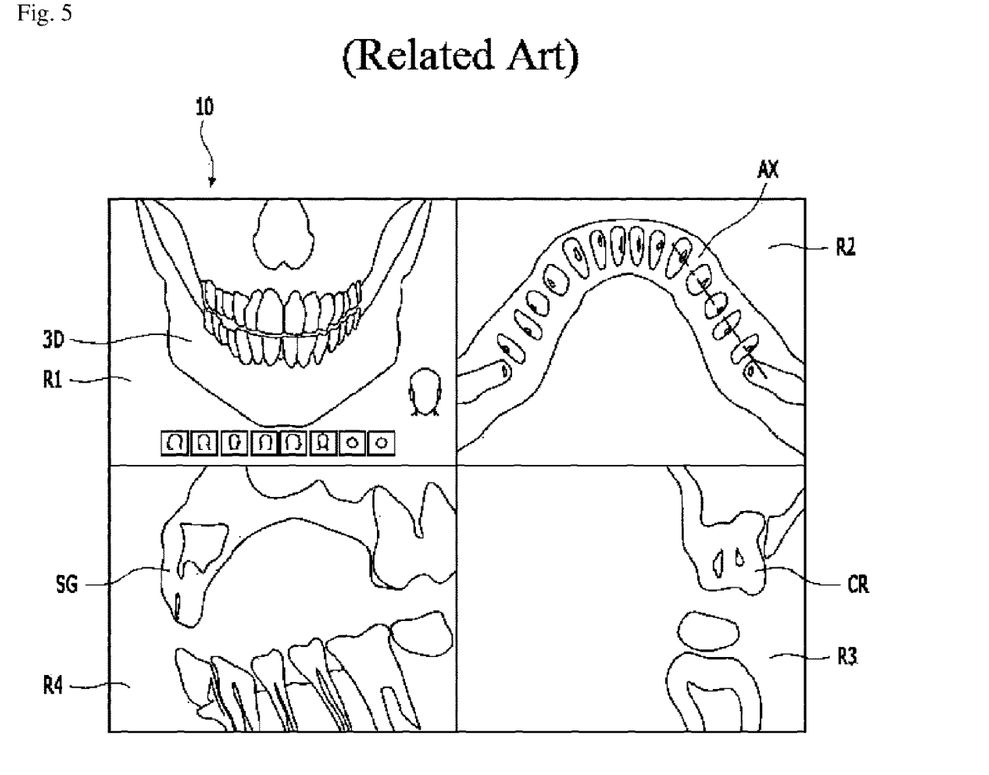
FIG. 5 is a schematic diagram showing a step of magnifying sectional images AX, CR and SG.
Figure 6:
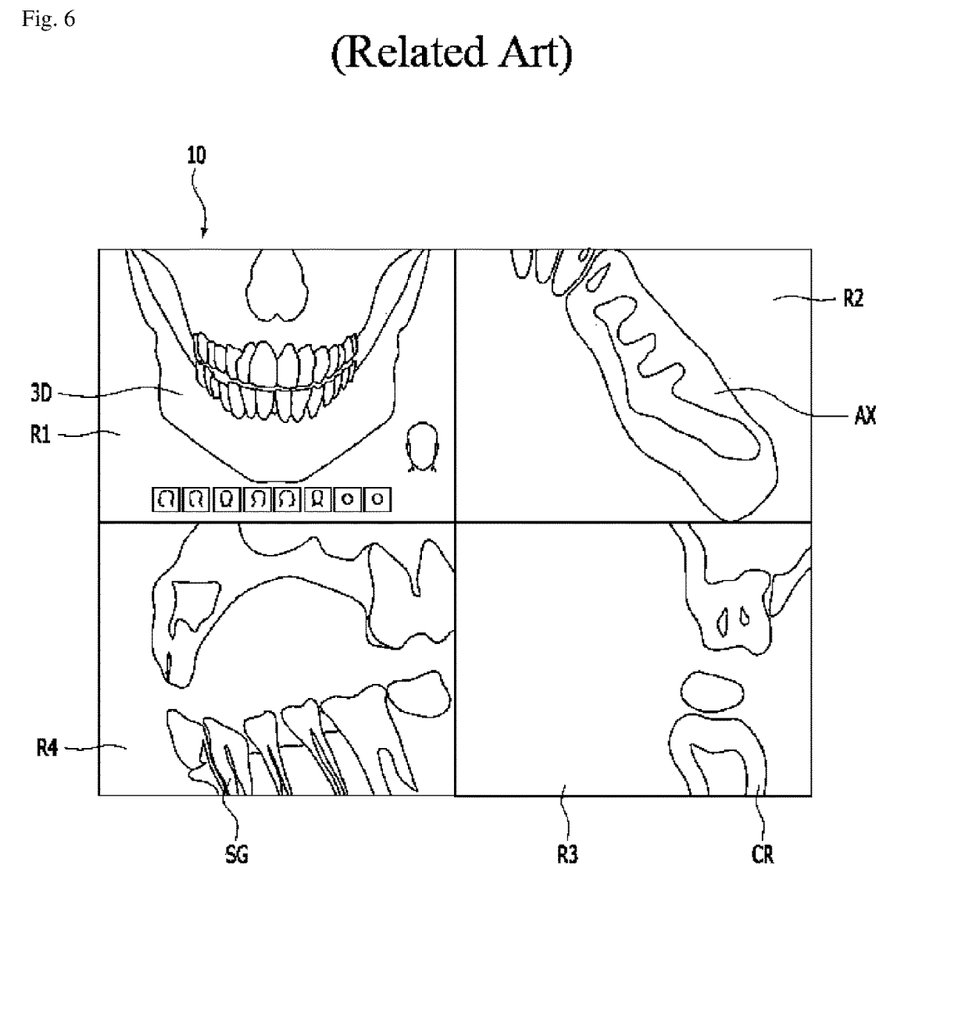
FIG. 6 to FIG. 8 are schematic diagrams showing movement of an axial image, a coronal image and a sagittal image in each display region.
Figure 7:
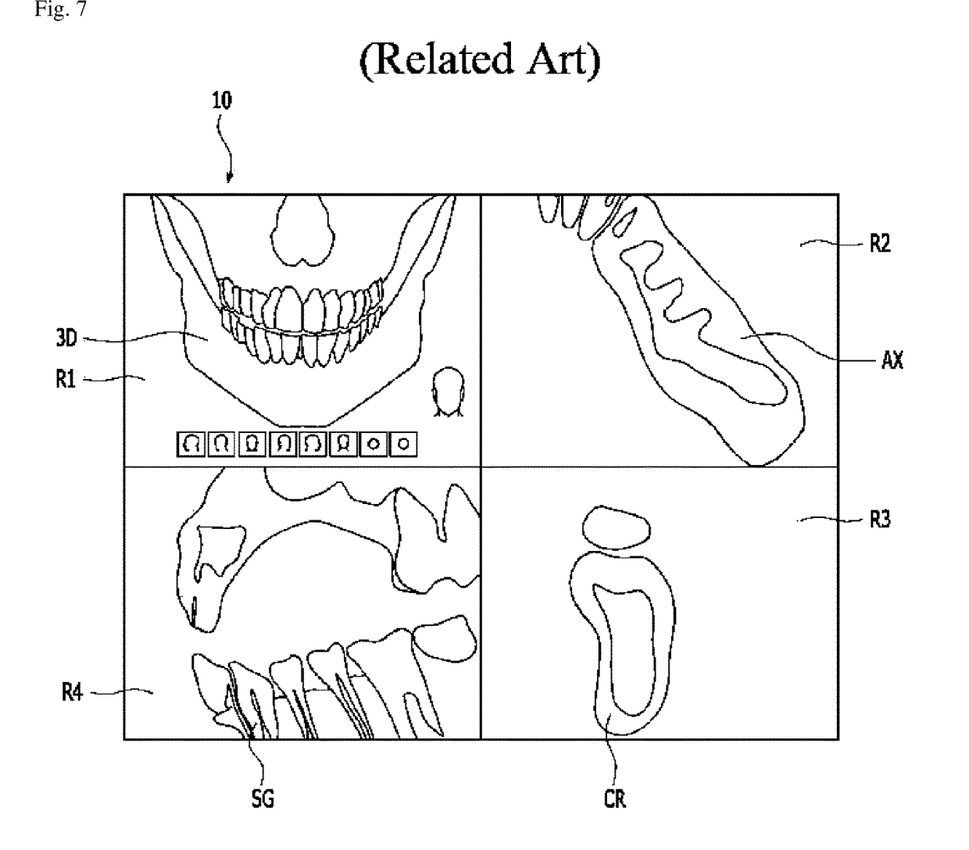
Figure 8:
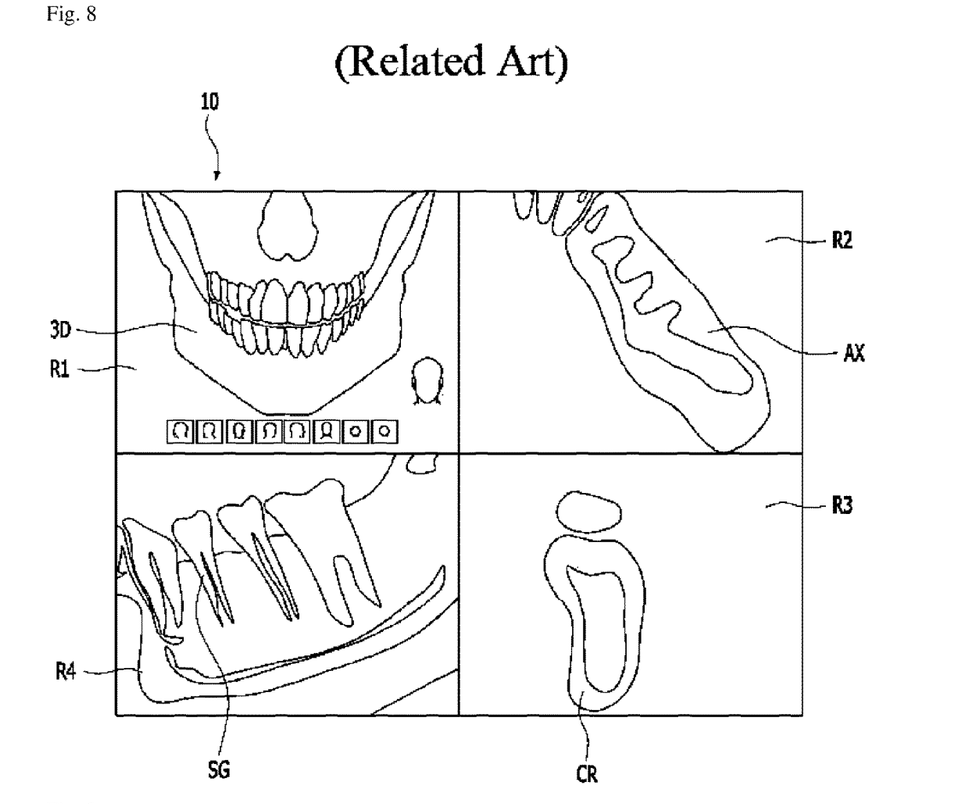

In order to changes the display conditions of each image, the user should perform at least seven steps as follows: i) specifying a height H of a tooth of interest on a coronal image CR (FIG. 2), ii) specifying a center C of the tooth of interest on the axial image AX (FIG. 3), iii) rotating one of two axes, perpendicular each other at the center C, by a rotating angle R, so that the axis becomes parallel to the tangent of a dental arch (FIG. 4), iv) magnifying the sectional images (FIG. 5), v) moving the axial image so that the tooth of interest is located on a center of the image display region R2 (FIG. 6), vi) moving the coronal image so that the teeth of interest is located on a center of the image display region R3 (FIG. 7), and vii) moving the sagittal image so that the teeth of interest is located on a center of the image display region R4 (FIG. 8).

As described above, the user performs a relatively large number of steps including rotating the axis, determining magnification ratio, moving the image in each display region, after selecting the teeth of interest, in order to observe the 3D image and the sectional images in association with one another. Further, the user should be a highly skilled person in the use of the image display device to generate the desired views. Even when used by an expert, is the large number of steps described above creates a disadvantage of losing time and possible error.

DISCLOSURE OF INVENTION

Technical Problem

Manipulation of an image, such as a dental image, between several views to focus on a particular area of one of the teeth in interest requires a user to perform many steps before obtaining the desired image. Such excessive steps in manipulation requires time, skill and training on the part of the user, and increases the possibility of error.

Solution to Problem

A volume image and related sectional images thereof may be shown in association with one another by arranging the designation point on the volume image and the corresponding points on the sectional images, rotating the volume image in consideration of the designation point and magnifying the sectional image concurrently.

In accordance with at least one embodiment, an image display apparatus may be provided for producing and displaying a 3D image and corresponding sectional images. The image display apparatus may include a data storage, an input interface, an image display, and a processor. The data storage may be configured to store image data. The input interface may be configured to receive position information of a first image point from a user. The image display may be configured to display, based on 3D image data and sectional image data, i) a three-dimensional (3D) image in a first display region of a screen, and ii) a sectional image of the 3D image in a second display region of the screen. The processor may be configured to generate, with the image data stored in the data storage unit, i) the 3D image data to display the 3D image by locating the first image point of the 3D image at a first position in the first display region and ii) the sectional image data to display the sectional image of the 3D image by locating a second image point of the sectional image at a second position in the second display region. The second image point may correspond to the first image point and the second position corresponds to the first position.

In accordance with at least one embodiment, a method may be provided for displaying images. The method may include displaying a second three-dimensional (3D) image in a first display region by locating a first image point of the second 3D image on a first position in the first display region of a screen and displaying sectional images of the second 3D image in a plurality of second display regions of the screen, respectively, by locating a second image point of each sectional image on a second position in each second display region. The second image points may be corresponding to the first image point and the second positions may be corresponding to the first position.

Advantageous Effects of Invention

A user does not require substantial skill or training to obtain appropriate images in association with one another for diagnosis and treatment, while also reducing the time required to obtain the desired image.

BRIEF DESCRIPTION OF DRAWINGS

The accompanying drawings, which are incorporated in and constitute a part of this specification, illustrate one or more embodiments described herein and, together with the description, explain these embodiments. In the drawings.

BEST MODE FOR CARRYING OUT THE INVENTION

An image display apparatus in accordance with the present invention includes: a data storage configured to store image data; an input interface configured to receive position information of a first image point from a user; an image display configured to display, based on 3D image data and sectional image data, i) a three-dimensional (3D) image in a first display region of a screen, and ii) a sectional image of the 3D image in a second display region of the screen; and a processor configured to generate, with the image data stored in the data storage, i) the 3D image data to display the 3D image by locating the first image point of the 3D image at a first position in the first display region and ii) the sectional image data to display the sectional image of the 3D image by locating a second image point of the sectional image at a second position in the second display region, wherein the second image point corresponds to the first image point and the second position corresponds to the first position.

Mode for the Invention

The following detailed description refers to the accompanying drawings. The same reference numbers in different drawings may identify the same or similar elements. Also, the following detailed description does not limit the invention.

In accordance with at least one embodiment, a display device may produce and display a 3D image of an object and corresponding sectional views based on an image point designated on a part of interest in the object. Particularly, the display device may detect single user input to designate an image point on a part (e.g., a tooth) of interest in an object. Based on the detected single user input, the display device may produce and display a 3D image and corresponding multiplanar reconstruction (MPR) views of the part of interest without requiring further user inputs or user interaction. Hereinafter, overall configuration and operation of such a display device will be described with reference to FIG. 9. For convenience and ease of understanding, the display device will be described as displaying a 3D image and corresponding sectional images of dental structures. However, the present invention is not limited thereto. The display device may be applied to producing and displaying 3D image and sectional views of any objects.

Figure 9:
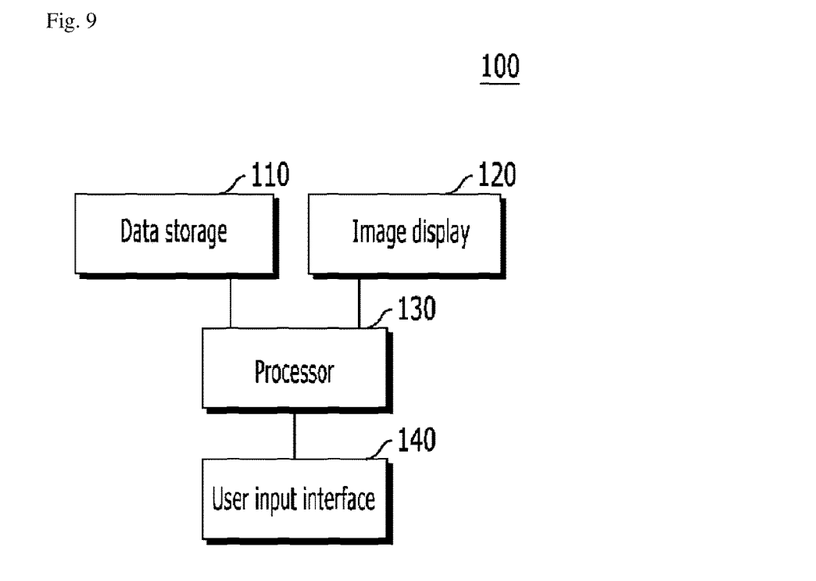
FIG. 9 is a schematic diagram showing a display device in accordance with at least one embodiment.

FIG. 9 illustrates a display device in accordance with at least one embodiment. Referring to FIG. 9, display device 100 displays a three-dimensional (3D) image and at least one sectional image in association with one another on a screen. Display device 100 may include data storage 110, image display 120, processor 130 and user input interface 140. Display device 100 may be configured and implemented via a typical computer.

Figure 10:
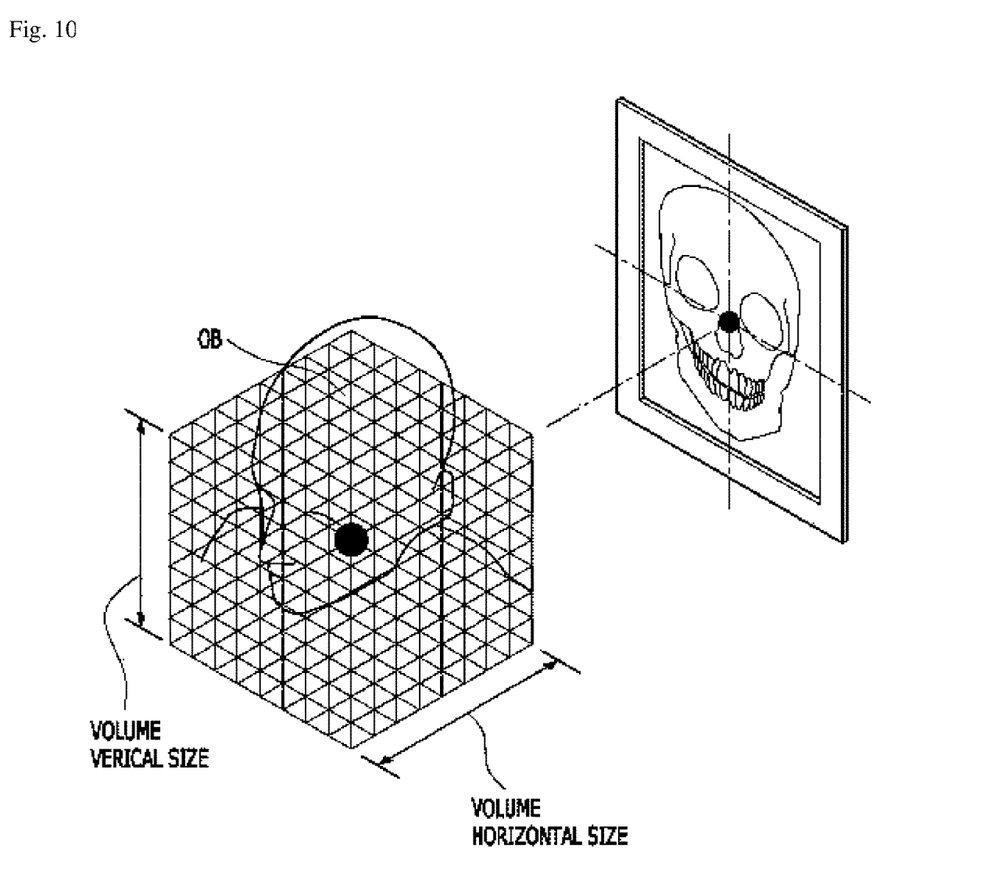
FIG. 10 and FIG. 11 are schematic diagrams for explaining image data of a CT image.

Data storage 110 may store 3D X-ray image data. The stored 3D X-ray image data may be generated based on image signals obtained from an X-ray CT imaging apparatus. As an example, FIG. 10 illustrates the generation of 3D X-ray image data. As shown in FIG. 10, image signals may be obtained by emitting an X-ray to an object (OB) and detecting the X-ray transmitted through the object (OB) using an X-ray detector. The obtained image signals may be processed to generate the 3D X-ray image data. After the generation of 3D X-ray image data, the 3D X-ray image data may be stored in data storage 110. The 3D X-ray image data may include information on voxel values and CT numbers (e.g., Hounsfield scale).

User input interface 140 represents one or more devices that allow a user to interact with display device 100 such as, but not limited to, touch screen input, mouse input, and keyboard input. Advantageously, some embodiments employ a mouse input to select portions of the images on the screen for further processing.

In accordance with at least one embodiment, user input interface 140 may receive a user input for designating an image point that indicates a part of interest in an object. For example, such a user input may be single mouse click that points a part of interest in an image displayed on a screen of image display 120. User input interface 140 may transfer such a user input to processor 130 to produce 3D image and corresponding section images in association with the image point made through the user input.

Processor 130 may produce a CT image of the object (OB) based on the 3D X-ray image data stored in data storage 110 and a user input detected by user input interface 140. The CT image may include a 3D image and corresponding sectional images. As described, the 3D X-ray image data may include information on voxel values and CT numbers (e.g., Hounsfield scale). Processor 130 may process such 3D X-ray image data and produces 3D image data for displaying a 3D image of an object and sectional image data for displaying a plurality of sectional images of the object.

For example, the sectional images may include an axial image, a coronal image, and a sagittal image.

Figure 11:
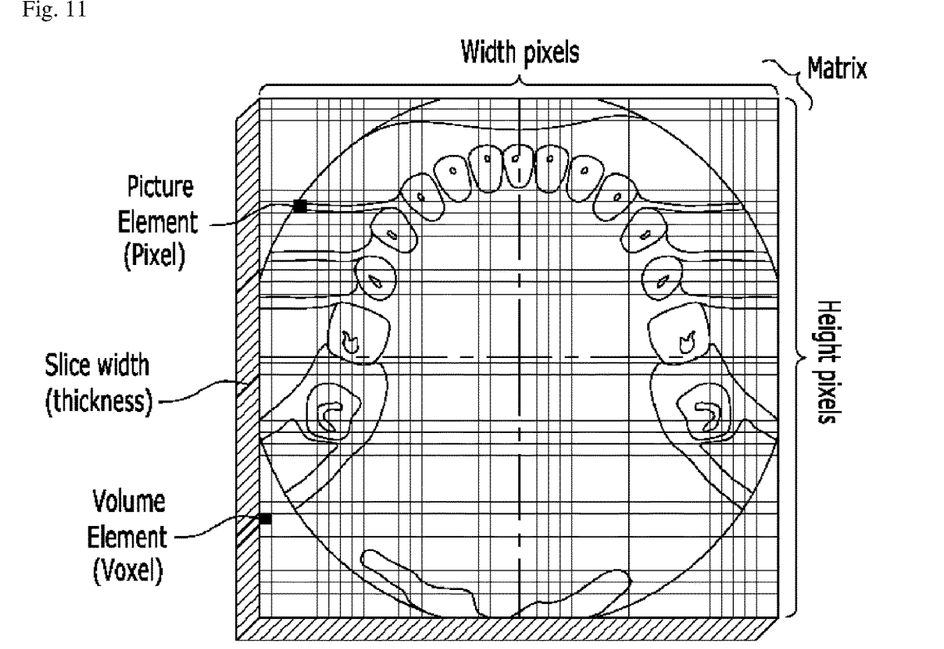

The sectional images may be referred to as multiplanar reconstruction views, the axial image may be referred to as an image of an axial plane view, the coronal image may be referred to as an image of a coronal plane view, and the sagittal image may be referred to as an image of a sagittal plane view or a transverse plane view. FIG. 11 illustrate an axial image created produced based on the 3D X-ray image data stored in data storage 110. Besides the axial image, processor 103 may produce the coronal images and the sagittal images directly or indirectly from the 3D X-ray Image data.

Processor 130 may also produce the 3D image and the corresponding sectional views at predetermined magnification ratios. Such magnification ratios may be stored in data storage 110. The magnification ratios may be initially determined by a system designer as a default magnification ratio or set by a user in response to a user input made through user input interface 140.

Image display 120 may receive the 3D image data and the sectional image data from processor 130 and display the 3D image and the sectional images. For example, image display 120 may display the 3D image data in a first display region and the sectional image data in at least one second display region. In accordance with at least one embodiment, image display 120 may provide first display region R1 for displaying a 3D image data and three second display regions R2, R3, and R4 for displaying sectional image data. However, the present invention is not limited thereto. Hereinafter, displaying a 3D image and corresponding sectional images on display unit 120 will be described with reference to FIG. 12.

Figure 12:
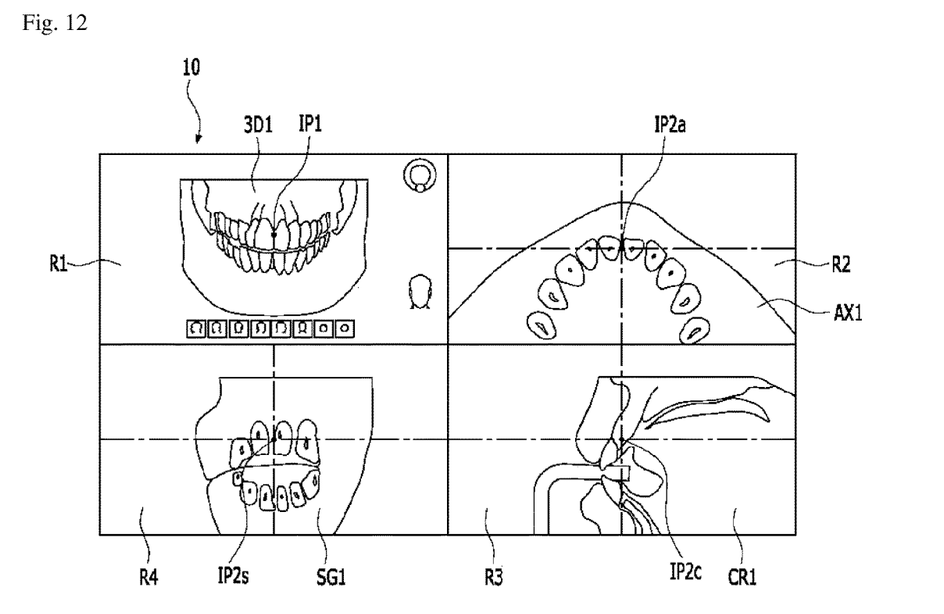
FIG. 12 is a schematic diagram showing displaying a 3D image and a plurality of sectional images in association with one another on a screen of a display unit in accordance with at least one embodiment.

FIG. 12 illustrates an image display that displays a 3D image and sectional images in accordance with at least one embodiment. Referring to FIG. 12, image display 120 may receive the 3D image data and form first volume X-ray image 3D1 within first display region R1 of screen 10 with first image point IP1 of volume X-ray image 3D1 positioned at a first position in first display region R1. Image display 120 may display first volume X-ray image 3D1 having a contour surface passing first image point IP1 in parallel to screen 10. That is, the contour surface passing first image point IP1 may face a user in front of screen 10. Namely, first image point IP1 is directed to the front direction of screen 10.

Furthermore, image display 120 may display a plurality of sectional images: axial image AX1, coronal image CR1, and sagittal image SG1, within a plurality of second display regions R2, R3, and R4, respectively. For example, image display 120 may form axial image AX1, coronal image CR1, and sagittal image SG1 based on first volume X-ray image 3D1 in different directions. Image display 120 may i) display axial image AX1 in display region R2 with image point IP2a at a second position of display region R2, ii) display coronal image CR1 in display region R3 with image point IP2c at a second position of display region R3 and iii) display sagittal image SG1 in display region R4 with image point IP2s at a second position of display region R4. Second image points IP2a, IP2c and IP2s correspond to first image point IP1, and the second positions correspond to the first position.

For example, if the first position is the center of the first display region R1, the second positions are also the centers of the display regions R2, R3 and R4, respectively. The cross sectional images in different directions may be displayed by predetermined magnification ratios which are stored in data storage 110. The stored magnification ratios may be a default magnification ration set by at least one of a system designer and a user. However, the present invention is not limited thereto. For example, a user may be allowed to input or to set the magnification ratio through user input interface 140. Desirably, the magnification ratios of all the sectional images are the same value, but the present invention is not limited thereto.

Processor 130 may generate the 3D image data with the 3D X-ray image data stored in data storage 110 so as to locate first image point IP1 on volume X-ray image 3D1 at a first position in first display region R1 and to change the display direction of the contour surface passing through first image point IP1 facing to a user. Such a contour surface passing through first image point IP1 may be displayed in parallel to screen 10. For example, processor 130 may produce 3D image data based on the 3D X-ray image data in data storage 110 and a user input detected by user input interface 140. The user input may be single mouse click that points a part of interest in a target object. Processor 130 may receive position information of the user input made through user input interface 140 and produce the 3D image data based on the position information to display an image part associated with first image point IP1 positioned at a first position of first display region R1. For example, the first position may be a center of first display region R1.

Processor 130 may also generate the sectional image data for displaying axial image AX1, coronal image CR1, and sagittal image SG1 so as to locate the second image points at second positions in the second display regions R2, R3, R4, respectively, which are corresponding to the first image point IP1. For example, the second positions may be a center of respective second display regions R2, R3, and R4, but the present invention is not limited thereto.

First image point IP1 may be designated by a user through user input interface 140 of display device 100. For example, a user designates first image point IP1 to point a part of interest in an object, (e.g., a tooth of interest in a dental structure). Such designation may be performed by pointing an image of a tooth of interest using an input device (e.g., a mouse). Such designation may be made by single user input such as single mouse click.

Second image points IP2a, IP2c and IP2s may be automatically designated to be located at the same tooth of interest in the respective sectional images corresponding to first image point IP1 in accordance with at least one embodiment. For example, processor 130 may calculate position information of second image points IP2a, IP2c, and IP2s based on position information of first image point IP1. Particularly, processor 130 may consider various characteristics of each sectional view (e.g., axial plane view, coronal plane view, and sagittal plane view). That is, although first image point IP1 indicates a contour surface of a tooth of interest, second image point IP2a of an axial plane view may not indicate the same contour surface of the tooth of interest. Second image point IP2a of the corresponding axial plane view may indicate a center axial plane of the same tooth of interest or an axial plane passing a top of a gum of the same tooth.

Furthermore, second image points IP2c and IP2s of the corresponding coronal plane view and the corresponding sagittal plane view may not indicate the same contour surface of the tooth of interest. For example, second image points IP2c and IP2s of the corresponding coronal plane view and the corresponding sagittal plane view may indicate a center coronal plane or a center sagittal plane of the same tooth of interest. Or, second image points IP2c and IP2s of the corresponding coronal plane view and the corresponding sagittal plane view may indicate a coronal plane or a sagittal plane passing an end of a root of the same tooth of interest. Such second image points IP2a, IP2c, and IP2s may be set by at least one of a system designer and a user.

As described, display device 100 may indicate single user input that designate first image point IP1 pointing a part of interest in a 3D image, automatically calculate second image points IP2a, IP2c, and IP2s pointing corresponding planes of the same part of interest in sectional images, and reconstruct the 3D image and the corresponding sectional images to show the relatively most interesting part and planes of the same part of interest without requiring further user inputs or user interactions. Hereinafter, an operation for designating a first image point and reconstructing a 3D image and corresponding sectional images based on the first image point will be described with reference to FIG. 13 to FIG. 15.

Figure 13:
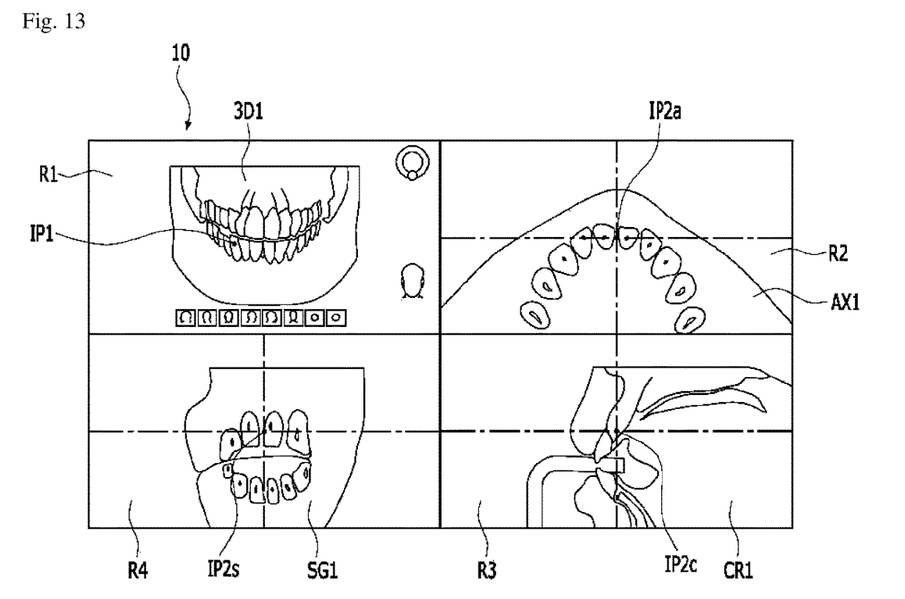
FIG. 13 is a schematic diagram showing a designation of a first image point IP1 on a 3D image displayed on a screen in accordance with at least one embodiment.
Figure 14:
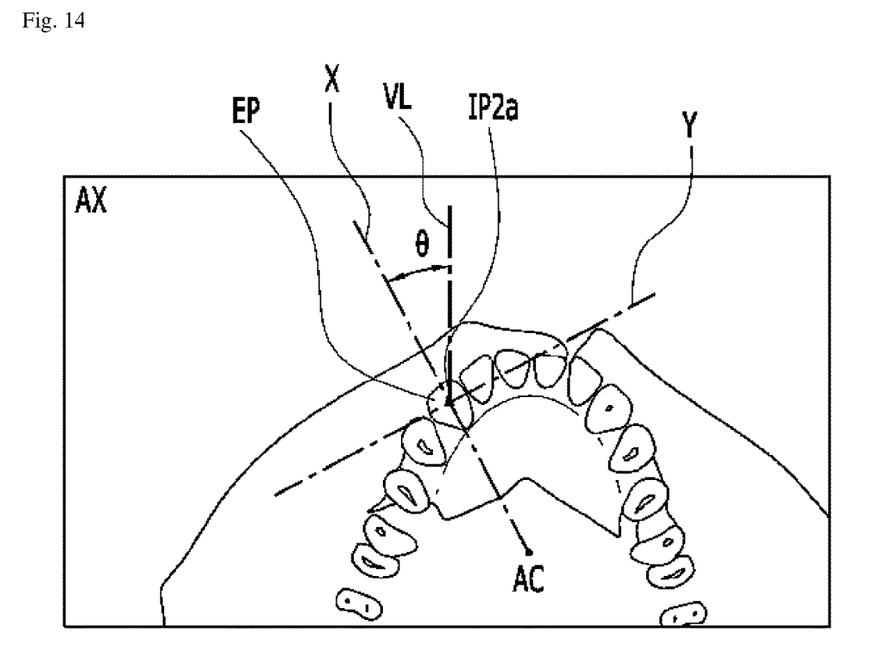
FIG. 14 is a schematic diagram for explaining a method of determining a second image point, a pair of axial axes and calculating a rotation angle O of the 3D image in accordance with at least one embodiment.
Figure 15:
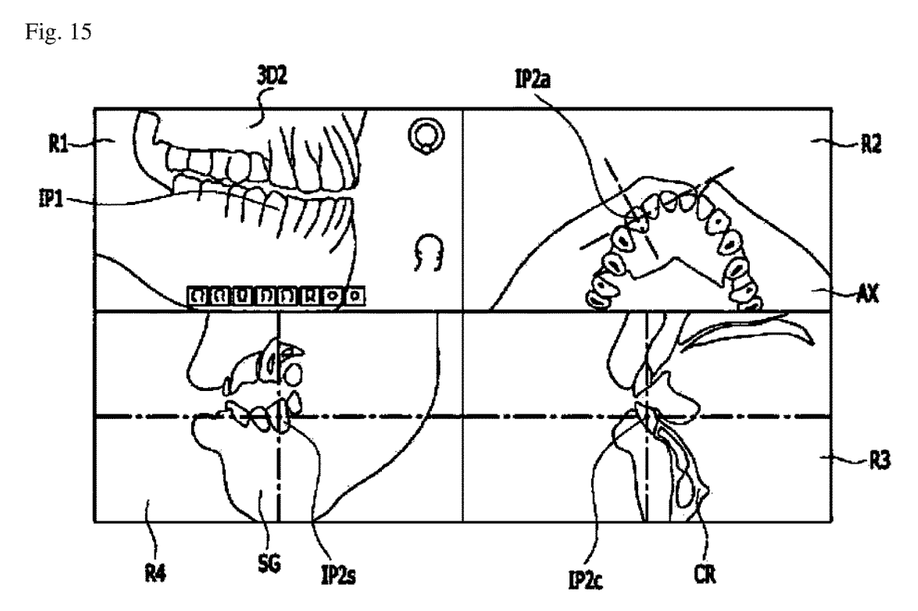
FIG. 15 is a schematic diagram showing displaying another 3D image and corresponding sectional images on a screen of a display device, after designation of a first image point IP1 on a previous 3D image, in accordance with at least one embodiment.

FIG. 13 illustrates designation of a first image point in accordance with at least one embodiment. FIG. 14 is a diagram for describing reconstructing an axial plane image based on a first image point in accordance with at least one embodiment. FIG. 15 illustrates displaying 3D image and corresponding sectional images, which are reconstructed based on a first image point designated by a user in accordance with at least one embodiment.

Referring to FIG. 13, screen 10 displays first volume image 3D1 in a first display direction (step 1). For example, processor 130 may produce first volume image 3D1 of a dental structure to show a contour surface of incisors. That is, image display 120 may display the contour surface of incisors in parallel to screen 10 (e.g., the first display direction).

First image point IP1 may be designated by a user on first volume image 3D1 (step 2). For example, a user might want to carefully examine a lower right cuspid. In this case, the user makes single user input to designate first image point IP1. That is, the user points the lower right cuspid using an input device (e.g., a mouse). Processor 130 may recognize such signal user input as designating first image point IP1 and obtain position information of first image point IP1 (e.g., the lower right cuspid).

Processing unit 130 may generate 3D image data for displaying second volume image 3D2 and sectional image data for displaying sectional images AX2, CR2, and SG2 of second volume image 3D2 (step 3).

Display unit 120 may display second volume image 3D2 so as to locate first image point P1 at a first position along a front direction in first display region R1 and the sectional images while locating the second image point IP2a, IP2b or IP2c at the second position corresponding to the first position with given magnification ratios or a magnification ratio input through user input interface 140 (step 4). Desirably, all of the sectional images may be displayed with the same magnification ratio. The displaying of second volume image 3D2 and the sectional images thereof may be displayed concurrently, or substantially simultaneously.

As described, display device 100 reconstructs a 3D image and corresponding sectional images based on first image point IP1 designated by single user input. Hereinafter, operation for generating sectional image data based on the first image point IP1 will be described in detail with reference to FIG. 14. Referring to FIG. 14, processor 130 may generate the sectional image data based on first image point IP1 made on a lower right cuspid of FIG. 13, as follows. i) Processor 130 may select an axial image (AX) (e.g., an axial plane view) showing a dental arch image at a height (e.g., a height value or a z axis value) of first image point IP1 designated by a user. ii) Processor 130 may analyze CT numbers of pixels of the axial image (AX), included in a virtual line drawn to pass first image point IP1 along the first display direction D1 on the axial image. Such a virtual line and the first display direction D1 may be identical to a vertical line (VL) shown in FIG. 14. The CT numbers of pixels may be referred to as voxel values or CT numbers of voxels.

iii) Processor 130 may determine edge point EP where the difference of CT numbers between two adjacent pixels (e.g., voxels) is maximum. iv) Processor 130 may determine second image point IP2a by finding a point that has CT numbers within a predetermined range and is apart from the edge point EP by a predetermined distance along the first direction D1. For example, the predetermined distance may be about 3 mm. v) Processor 130 may establish a pair of axial axes X and Y perpendicular to each other at second image point IP2a on the axial image (AX), and establish a pair of axes for a coronal image and a sagittal image, respectively, on the basis of the pair of axial axes. vi) Processor 130 may determine a rotation angle O.

vii) Processor 130 may generate sectional image data based on each pair of the axes. The axial axes X and Y may be determined fixing the direction of the axial axis X toward to a center of dental arch AC as shown in FIG. 14, but the present invention is not limited thereto. In accordance with another embodiment, the axial axis Y may be determined with a tangential line to the dental arch AC at second image point IP2a. In case of fixing the direction of the axis X, the rotation angel is determined with an angle between the axis X and a vertical line (VL) of screen 10. In FIG. 14, the vertical line (VL) of screen 10 may be identical to the first display direction D1 since they are in parallel. In case of fixing the direction of the axis Y, the rotation angle may be determined with an angle between the axis Y and a horizontal line of the screen 10. The procedures related to FIG. 14 will not be shown on screen 10, but are only exemplary for illustrating examples of procedures to be performed by and within the (e.g., digital) processor 130.

Once first image point IP1 is designated on first volume image 3D1 by the user through user input interface 140, processing unit 130 may generate the 3D image data for second volume image 3D2 and the sectional image data in accordance with at least one embodiment, as described above. As shown in FIG. 15, image display 120 may display the four images: second volume image 3D2, axial image AX2, coronal image CR2, and sagittal image SG2 in respective display regions R1, R2, R3, and R4. As described, when the user designates only single image point (e.g., first image point IP1) with single user input, display device 100 automatically rotates the 3D image and rearranges the corresponding sectional images thereof on corresponding positions with respect to the first image with the predetermined magnification by automatically calculating second image points IP2a, IP2c, and IP2s based on first image point IP1 in accordance with at least one embodiment.

According to embodiments of this invention, the volume image and the sectional images thereof may be shown in association with one another by arranging the designation point on the volume image and the corresponding points on the sectional images, rotating the volume image in consideration of the designation point and magnifying the sectional image concurrently. Thus, the user does not require substantial skill or training to obtain appropriate images in association with one another for diagnosis and time for obtain appropriate can be reduced effectively.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implentation."

As used in this application, the word exemplary is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or rather than an exclusive "or" That is, unless specified otherwise, or clear from context, "employs A or B" is intended to mean any of the natural inclusive permutations. That is, if X employs A; X employs B; or X employs both A and B, then X employs A or B is satisfied under any of the foregoing instances. In addition, the articles "a" and "an" as used in this application and the appended claims should generally be construed to mean "one or more unless specified otherwise or clear from context to be directed to a singular form.

Moreover, the terms "system," "component," "module," "interface," "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The present invention can be embodied in the form of methods and apparatuses for practicing those methods. The present invention can also be embodied in the form of program code embodied in tangible media, non-transitory media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium, etc., generated using a method and/or an apparatus of the present invention.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

Although embodiments of the present invention have been described herein, it should be understood that the foregoing embodiments and advantages are merely examples and are not to be construed as limiting the present invention or the scope of the claims. Numerous other modifications and embodiments can be devised by those skilled in the art that will fall within the spirit and scope of the principles of this disclosure, and the present teaching can also be readily applied to other types of apparatuses. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

INDUSTRIAL APPLICABILITY

The present invention may be applied to display a three-dimensional image and sectional images concurrently in defined relation.

The invention claimed is:
1. An image display apparatus comprising:
 a data storage configured to store image data of a target object, three-dimensional (3D) image data produced based on the image data to display a 3D image of the target object, and sectional image data produced based on the image data to display a sectional image of the 3D image;
 an image display configured to display i) the 3D image in a first display region and ii) the sectional image of the 3D image in a second display region;
 an input interface configured to receive position information of a first image point from a user, wherein the first image point designates a point-of-interest in at least one of the 3D image and the sectional images; and
 a processor configured to generate, with the image data stored in the data storage, i) the 3D image data to display the point-of-interest of the 3D image at a first position of the first display region by rearranging the 3D image data based on image data associated with the first image point and ii) the sectional image data to display the point-of-interest of the sectional image at a second position in the second display region by rearranging the sectional image data based on image data associated with the first image point,
 wherein the second position corresponds to the first position.
2. An image display apparatus according to claim 1, wherein the processor is configured to generate the 3D image data to display the point-of-interest of the 3D image, indicated by the first image point, to be directed to a front direction of the image display.

3. An image display apparatus according to claim 2, wherein the sectional image data is generated for displaying the sectional images with the same magnification ratio.

4. An image display apparatus according to claim 3, wherein the first position and the second position are center points in the first display region and the second display region, respectively.

5. An image display apparatus according to claim 1, wherein the sectional image data is generated for displaying the sectional image with the same magnification ratio.

6. An image display apparatus according to claim 1, wherein:
the data storage stores 3D X-ray image data of a dental arch including teeth; and
the 3D image is a 3D X-ray image of the dental arch.

7. An image display apparatus according to claim 6, wherein the sectional image includes at least one of an axial image, a coronal image, and a sagittal image.

8. An image display apparatus according to claim 7, wherein the first image point is a point on a tooth of interest.

9. An image display apparatus according to claim 6, wherein the image display displays the 3D image and the sectional image at the same time, substantially.

10. An image display apparatus according to claim 1, wherein the first position and the second position are center points in the first display region and the second display region, respectively.

11. A method of displaying images, comprising:
receiving position information of an image point from a user, wherein the image point designates a point-of-interest of at least one of the images;
displaying a second three-dimensional (3D) image in a first display region with the point-of-interest of the 3D image located at a first position in the first display region by rearranging 3D image data based on image data associated with the image point; and
displaying sectional images of the second 3D image in a plurality of second display regions of the screen, respectively, with the point-of-interest of each one of the sectional images at a second position in each second display region by rearranging sectional image data based on image data associated with the image point,
wherein the second positions are corresponding to the first position.

12. A method of displaying images according to claim 11, wherein a part of the 3D image, indicated by the image point, is displayed to be directed to a frontal direction of the screen.

13. A method of displaying images according to claim 12, wherein the sectional images are displayed with the same magnification ratio.

14. A method of displaying images according to claim 11, wherein the sectional images are displayed with the same magnification ratio.

15. A method of displaying images according to claim 11, wherein the 3D image is a 3D X-ray image of a dental arch.

16. A method of displaying images according to claim 15, wherein the sectional images include an axial image, a coronal image, and a sagittal image.

17. A method of displaying images according to claim 16, wherein the image point is a point on a tooth of interest.

18. A method of displaying images according to claim 15, wherein the displaying of the 3D image and the displaying of the sectional images are concurrent.

19. A method of displaying images according to claim 11, wherein the first position and the second position are center points in the first display region and the second display region, respectively.

20. A non-transitory machine-readable storage medium, having encoded thereon program code, wherein, when the program code is executed by a machine, the machine implements a method for display images, comprising the steps of:
receiving position information of an image point from a user, wherein the image point designate a point-of-interest of at least one of the images;
displaying a second three-dimensional (3D) image in a first display region with the point-of-interest of the 3D image located at a first position in the first display region by rearranging 3D image data based on image data associated with the image point; and
displaying sectional images of the second 3D image in a plurality of second display regions of the screen, respectively, with the point-of-interest of each one of the sectional images at a second position in each section display region by rearranging sectional image data based on image data associated with the image point,
wherein the second positions are corresponding to the first position.

* * * * *